(12) United States Patent
Mouhat et al.

(10) Patent No.: US 7,745,575 B1
(45) Date of Patent: Jun. 29, 2010

(54) OSK1 DERIVATIVES

(75) Inventors: Stephanie Mouhat, Chelles (FR);
Jean-Marc Sabatier, Rousset (FR);
Bonabes Olivier de Rouge, Paris (FR)

(73) Assignee: Cellpep Pharma Inc. (CA)

( * ) Notice: Subject to any disclaimer, the term of this patent is extended or adjusted under 35 U.S.C. 154(b) by 28 days.

(21) Appl. No.: 11/571,005

(22) PCT Filed: Jun. 27, 2005

(86) PCT No.: PCT/EP2005/006897
§ 371 (c)(1),
(2), (4) Date: Dec. 10, 2007

(87) PCT Pub. No.: WO2006/002850
PCT Pub. Date: Jan. 12, 2006

(30) Foreign Application Priority Data
Jun. 25, 2004 (GB) ................... 0414272.5

(51) Int. Cl.
*C07K 14/00* (2006.01)
(52) U.S. Cl. ........................................ 530/324; 514/12
(58) Field of Classification Search ................ 530/324; 514/12
See application file for complete search history.

(56) References Cited
U.S. PATENT DOCUMENTS
2004/0039167 A1 2/2004 Sabatier et al.
2007/0071764 A1* 3/2007 Sullivan et al. .......... 424/178.1

OTHER PUBLICATIONS

English Abstract of WO 99/018123, issued 1999.*
Jaravine Victor et al., "Three-dimensional structure of toxin OSK1 from Orthochirus scrobiculosus scorpion venom", Biochemistry, vol. 36, No. 6, pp. 1223-1232 (1997).
Huys, Isabelle et al., "Evidence for a function-specific mutation in the neurotoxin, parabutoxin 3", European Journal of Neuroscience, vol. 17, No. 9, pp. 1786-1792 (2003).
Lanigan, M. D. et al., "Designed peptide analogues of the potassium channel blocker ShK toxin," Biochemistry, American Chemical Society, vol. 40, No. 51 (2001).
Mouhat, Stephanie et al., "K+ channel types targeted by synthetic OSK1, a toxin from *Orthochirus scrobiculosus* scorpion venom," Biochemical Journal, vol. 385, No. part 1, pp. 95-104 (2005).
Tytgat et al., "A unified nomenclature for short-chain peptides isolated from scorpion venoms: a-KTx molecular subfamilies," Trends Pharmacol. Sci., 20(11), pp. 444-447 (1999).

* cited by examiner

Primary Examiner—David Lukton
(74) Attorney, Agent, or Firm—Clark & Elbing LLP

(57) ABSTRACT

OsK1 is a 38-residue peptide with 3 disulphide bridges and is found in the venom of the scorpion *Orthochirus scrobiculosus*. It is potently active on voltage-gated $K^+$ channels Kv1.1, Kv1.2 and Kv1.3, and moderately active on the type 1 intermediate-conductance $Ca^{2+}$-activated channel $K_{Ca}3.1$. Derivatives of OsK1, particularly involving truncation or point mutations, have been developed to enhance the activity against and selectivity for the Kv1.3 channel. This renders the derivatives likely candidates for the treatment of autoimmune diseases, including multiple sclerosis. Such use may be alone or in combination therapy with maurotoxin, another scorpion toxin.

6 Claims, 1 Drawing Sheet

OSK1 DERIVATIVES

CROSS REFERENCE TO PRIOR APPLICATIONS

This application is the U.S. national phase of International Application No. PCT/EP2005/006897 filed Jun. 27, 2005, which claims priority from Great Britain Application Serial No. 0414272.5 filed Jun. 25, 2004.

REFERENCE TO SEQUENCE LISTING

A Sequence Listing is provided in this patent document as a .txt file entitled, "50538_018001_Sequence_Listing," modified Jan. 12, 2010 (size: 21.7 KB).

The content of this file is herein incorporated by reference.

The invention relates to derivatives of OsK1 and to pharmaceutical compositions containing them. The derivatives are useful in the treatment of neurological disorders including multiple sclerosis.

BACKGROUND

OsK1 is a 38-residue peptide with 3 disulphide bridges and is found in the venom of the scorpion *Orthochirus scrobiculosus*. It is one of a number of short chain scorpion toxins which contain between 29 and 39 amino acid residues, are crosslinked by 3 or 4 disulphide bridges and are active on several potassium channel subtypes, both voltage gated and calcium activated. These short chain scorpion toxins have been classified by Tytgat et al., Trends Pharmacol. Sci., 20(11), 444-447, 1999. OsK1 is a group 3 toxin and is shown below in Table 1 along with the other group 3 toxins and one group 6 toxin, Maurotoxin (MTx).

TABLE 1

| | | |
|---|---|---|
| 3.1 | KTx | GVEINVKCSGSPQCLKPCKDA-GMR-FGKCMNR-KCHCTPK |
| 3.2 | AgTx2 | GVPINVSCTGSPQCIKPCKDA-GMR-FGKCMNR-KCHCTPK |
| 3.3 | AgTx3 | GVPINVPCTGSPQCIKPCKDA-GMR-FGKCMNR-KCHCTPK |
| 3.4 | AgTx1 | GVPINVKCTGSPQCLKPCKDA-GMR-FGKCING-KCHCTPK |
| 3.5 | KTx2 | VRIPVSCKHSGQCLKPCKDA-GMR-FGKCMNR-KCDCTPK |
| 3.6 | BmKTx | VGINVKCKHSGQCLKPCKDA-GMR-FGKCING-KCDCTPK |
| 3.7 | OsK1 | GVIINVKCKISRQCLEPCKKA-GMR-FGKCMNG-KCHCTPK |
| 3.8 | Bs6 | GVPINVKCRGSPQCIQPCRDA-GMR-FGKCMNG-KCHCTPQ |
| 6.2 | MTx | VSCTGSKDCYAPCRKQTGCPNA-KCINK-SCKCYGC |

Both the mammalian voltage-gated $K^+$ channel Kv1.3 and the type 1 intermediate-conductance $Ca^{2+}$-activated channel $K_{Ca}3.1$ (also referred to as IK1) are expressed in immune T-cells. Their relative abundance at the T-cell surface depends on the state of lymphocyte activation and differentiation. The potassium channel phenotype varies during the progression from the resting to the activated T-cell state, and from naive to effector memory T-cells. Therefore, blockers of these channel types possess potent immunomodulatory properties that could be beneficial in the treatment of human diseases, such as multiple sclerosis. Multiple sclerosis is a chronic inflammatory autoimmune disease of the central nervous system, characterised by progressive demyelination and axonal damage caused by reactive autoimmune lymphocytes. Activation and proliferation of these cells (effector memory T-cells) relies upon Kv1.3 channels (and possibly IK1 channels), and can be blocked by Kv1.3 channel blockers. Demyelination also involves unmasking of the Kv1.1 and Kv1.2 subtypes, which provokes leak currents and a decrease in nervous transmission (by altering the action potential).

We have found that OsK1, alone amongst the short chain scorpion toxins, is potently active on Kv1.1, Kv1.2 and Kv1.3 channels, and moderately active on IK1. It would be desirable to find synthetic peptides which retain or enhance this property- or part of this property- and/or block more potently the IK1 subtype.

Such derivatives may also be useful against other human disorders, such as graft rejection, rheumatoid arthritis, bone degradation, and cancer (abnormal cell proliferation).

THE INVENTION

Figure 1:
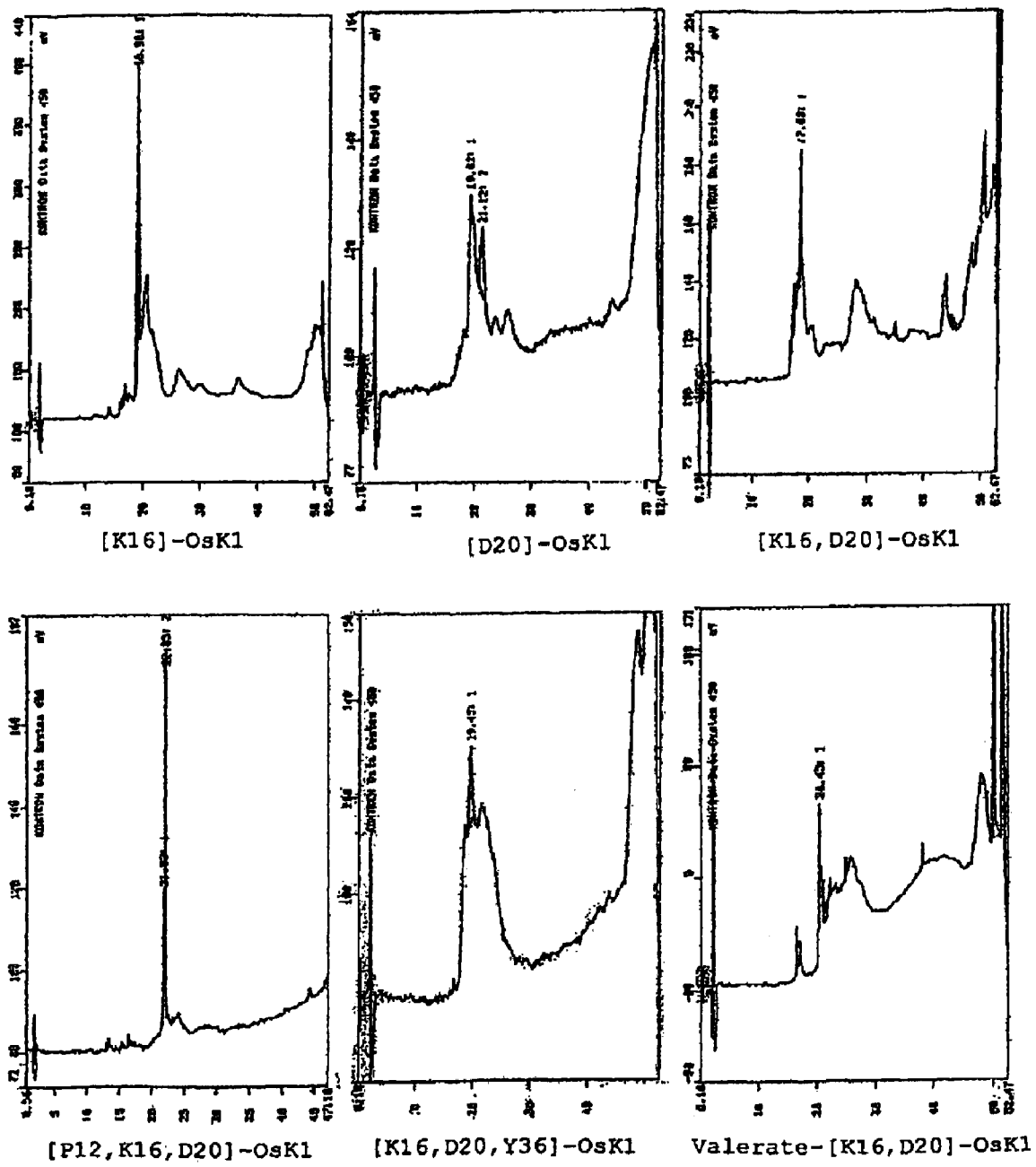
FIG. 1 is a series of HPLC profiles of Osk1 derivatives.

The invention provides an OsK1 derivative in which up to seven N-terminal amino acid residues have been omitted and/or in which up to four amino acid residues have been point mutated. Preferably, the replacement amino acid residue(s) are in positions 8 to 38 and occur in the corresponding position in another group 3 short chain scorpion toxin or in maurotoxin.

Table 2 lists the OsK1 derivatives which the inventors have studied. Not all of them are within the scope of the invention. Differences from OsK1 are shown in bold. It will be understood that $\Delta^n$ indicates that the peptide present in position n in OsK1 has been omitted and that r indicates that the peptide present in position n in OsK1 has been replaced with a peptide X. Ac stands for acetyl and Val for valeryl.

A preferred peptide is $[K^{16},D^{20}]$-OsK1 and this has been abbreviated as AOsK1. The substitution of lysine for glutamic acid at position 16 in OsK1 and of aspartic acid for lysine at position 20 in OsK1 follow the norms in those positions in kaliotoxins 1 and 2, agitoxins 1, 2 and 3 and *Buthus martensi* kaliotoxin. AOsK1 is about five times more potent on the Kv1.3 channel than OsK1 itself and is the most potent Kv1.3 channel blocker characterized so far. Since AOsK1 also shares the same activity on IK1, it makes this derivative a better lead compound than OsK1.

TABLE 2

| | |
|---|---|
| OsK1 | GVIINVKCKISRQCLEPCKKAGMRFGKCMNGKCHCTPK-$_{OH}$ |
| OsK1-NH$_2$ | GVIINVKCKISRQCLEPCKKAGMRFGKCMNGKCHCTPK-$_{NH2}$ |
| Ac-OsK1-NH$_2$ | Ac-GVIINVKCKISRQCLEPCKKAGMRFGKCMNGKCHCTPK-$_{NH2}$ |
| [$\Delta^1$]-OsK1-NH$_2$ | -VIINVKCKISRQCLEPCKKAGMRFGKCMNGKCHCTPK-$_{NH2}$ |

TABLE 2-continued

| | |
|---|---|
| [A³⁴]-OsK1 | GVIINVKCKISRQCLEPCKKAGMRFGKCMNGKCACTPK-$_{OH}$ |
| [K¹⁶]-OsK1 | GVIINVKCKISRQCLKPCKKAGMRFGKCMNGKCHCTPK-$_{OH}$ |
| [D²⁰]-OsK1 | GVIINVKCKISRQCLEPCKDAGMRFGKCMNGKCHCTPK-$_{OH}$ |
| AOsK1 | GVIINVKCKISRQCLKPCKDAGMRFGKCMNGKCHCTPK-$_{OH}$ |
| Val-AOsK1 | Val-GVIINVKCKISRQCLKPCKDAGMRFGKCMNGKCHCTPK-$_{OH}$ |
| AOsK1-NH₂ | GVIINVKCKISRQCLKPCKDAGMRFGKCMNGKCHCTPK-$_{NH2}$ |
| [Δ¹]-AOsK1 | -VIINVKCKISRQCLKPCKDAGMRFGKCMNGKCHCTPK-$_{OH}$ |
| [Δ¹]-AOsK1-NH₂ | -VIINVKCKISRQCLKPCKDAGMRFGKCMNGKCHCTPK-$_{NH2}$ |
| [Δ¹,T²]-AOsK1 | -TIINVKCKISRQCLKPCKDAGMRFGKCMNGKCHCTPK-$_{OH}$ |
| [Δ¹⁻⁴]-AOsK1 | ----NVKCKISRQCLKPCKDAGMRFGKCMNGKCHCTPK-$_{OH}$ |
| [Δ¹⁻⁶]-AOsK1 | ------KCKISRQCLKPCKDAGMRFGKCMNGKCHCTPK-$_{OH}$ |
| [Δ¹⁻⁷]-AOsK1 | -------CKISRQCLKPCKDAGMRFGKCMNGKCHCTPK-$_{OH}$ |
| [Δ³⁶⁻³⁸]-AOsK1 | GVIINVKCKISRQCLKPCKDAGMRFGKCMNGKCHC----$_{OH}$ |
| [K³]-AOsK1-NH₂ | GVKINVKCKISRQCLKPCKDAGMRFGKCMNGKCHCTPK-$_{NH2}$ |
| [P¹²]-AOsK1 | GVIINVKCKISPQCLKPCKDAGMRFGKCMNGKCHCTPK-$_{OH}$ |
| [N²⁵]-AOsK1 | GVIINVKCKISRQCLKPCKDAGMRNGKCMNGKCHCTPK-$_{OH}$ |
| [R³¹]-AOsK1 | GVIINVKCKISRQCLKPCKDAGMRFGKCMNRKCHCTPK-$_{OH}$ |
| [Y³⁶]-AOsK1 | GVIINVKCKISRQCLKPCKDAGMRFGKCMNGKCHCYPK-$_{OH}$ |
| Ac-[K¹²,R¹⁹]-AOsK1 | Ac-GVIINVKCKISKQCLKPCRDAGMRFGKCMNGKCHCTPK-$_{OH}$ |

Truncating the N-terminal of OsK1 or its derivatives reduces the activity of the resultant peptide against the Kv1.2 channel and, to a lesser extent, against the Kv1.1 channel, and therefore enhances the selectivity of the resultant peptide for the Kv1.3 channel. Further, truncating the N-terminal of OsK1 or its derivatives reduces the toxicity of the resultant peptide, possibly due to the decreased affinity towards the Kv1.1 and Kv1.2 channels. By contrast, truncating the C-terminal caused significant loss of activity against all channels measured.

A point mutation at position 2 of AOsK1, coupled with the omission of the peptide at position 1, gave a peptide [Δ¹,T²]-AOsK1 possessing an N-terminal domain (i.e. TIINVK) that is identical to those of margatoxin and noxiustoxin, two scorpion toxins potently active on Kv1.3 channel. The peptides truncated at the N-terminal, whether or not mutated at position 2, showed good activity against the Kv3.2 channel.

Docking studies have indicated that His in position 34 of OsK1 appeared to be involved in Kv1.2 and Kv1.3 docking, so replacement of this peptide, e.g. by Ala, is desirable, leading to higher selectivity for Kv1.3. Such studies have also suggested the inclusion of Lys at position 3 in place of Ile.

Asparagine at position 25 has been reported as important in the affinity of toxins with the Kv1.3 channel and arginine at position 31 is homologous with other toxins active on the Kv1.3 channel. In fact R at position 31 provides an AOsK1 derivative which has strong affinity to all of the Kv1.1, Kv1.2 and Kv1.3 channels.

OsK1 derivatives according to the invention may be acetylated at the N-terminal or may be amidated at the C-terminal in conventional manner. Another approach is to terminate the OsK1 derivative with a fatty acid having from 4 to 10 carbon atoms and from 0 to 2 carbon-carbon double bonds, or a derivative thereof such as an ω-amino-fatty acid. Either the N-terminal or the C-terminal may be so terminated. This should result in increased water solubility for the derivative, and enhanced bioavailability. The preferred fatty acid is valeric acid (or, for the C-terminal, ω-amino-valeric acid).

The invention further provides a pharmaceutical composition comprising an OsK1 derivative as described above in admixture with a pharmaceutically acceptable diluent or carrier.

Furthermore, the invention also provides the use of OsK1 or of an OsK1 derivative as described above for the preparation of a medicament for the treatment of autoimmume diseases, including but not limited to multiple sclerosis.

Maurotoxin is the most potent inhibitor amongst the short chain scorpion toxins of the calcium activated potassium channel subtype IK1. Replacing amino acid residue(s) occurring in the corresponding position(s) in maurotoxin may lead to the derivative having an enhanced activity against IK1 although the replacement is tyrosine for threonine at position 36 has not been shown to achieve this. In the absence of a single compound combining high activity on Kv1.3 with improved activity on IK1, we have investigated the possibility of combination therapy using an OsK1 derivative according to the invention with MTx. As shown below, the use of AOsK1 and MTx together does appear to be better than the use of either alone. Such combination therapy is thus included within the invention.

EXPERIMENTAL

OsK1 and the OsK1 derivatives listed in Table 2 were prepared by chemical synthesis using a peptide synthesizer (Model 433A, Applied Biosystems Inc.). Peptide chains were assembled stepwise on 0.25 mmol of HMP resin (1% cross-linked; 0.65 mmol of amino group/g) using 1 mmol of $N^\alpha$-(9-fluorenyl)methyloxycarbonyl (Fmoc) L-amino acid derivatives. Side chain-protecting groups for trifunctional residues were: trityl for cysteine, asparagine, histidine and glutamine; t-butyl for serine, threonine, tyrosine, aspartate and glutamate; 2,2,4,6,7-pentamethyldihydrobenzofuran-5-sulfonyl for arginine; and t-butyloxycarbonyl for lysine. $N^\alpha$-amino groups were deprotected by successively treating with 18 and 20% (v/v) piperidine/N-methylpyrrolidone for 3 and 8 min, respectively. After three washes with N-methylpyrrolidone, the Fmoc-amino acid derivatives were coupled (20 min) as their hydroxybenzotriazole active esters in N-methylpyrrolidone (4-fold excess). After peptides were assembled, and removal of N-terminal Fmoc groups, the peptide resins (ca. 1.5 g) were treated under stirring for 3 h at 25° C. with mixtures of trifluoroacetic acid/$H_2O$/thioanisole/ethanedithiol (73:11:11:5, v/v) in the presence of crystalline phenol (2.1 g) in final volumes of 30 ml per gram of peptide resins. The peptide mixtures were filtered, precipitated and washed twice with cold diethyloxide. The crude peptides were pelleted by centrifugation (3,200×g; 8 min). The crude peptides were then dissolved in $H_2O$ and freeze dried. Reduced AOsK1 analogues were solubilized at a concentration of ca. 0.6 mM in 0.2 M Tris-HCl buffer (pH 8.3) for oxidative folding (40 to 120 h depending on the peptide, 20° C.). The folded/oxidized peptides were purified to homogeneity by reversed-phase high pressure liquid chromatography (HPLC) ($C_{18}$ Aquapore ODS, 20 µm, 250×10 mm; PerkinElmer Life Sciences) by means of a 60-min linear gradient of 0.08% (v/v) trifluoroacetic acid/$H_2O$ (buffer A) with 0 to 40% of 0.1% (v/v) trifluoroacetic acid/acetonitrile (buffer B), at a flow rate of 6 ml/min (λ=230 nm). The purity and identity of each peptide were assessed by: (i) analytical $C_{18}$ reversed-phase HPLC ($C_{18}$ Lichrospher 5 µm, 4×200 mm; Merck) using a 60 min linear gradient of buffer A with 0-60% of buffer B, at a flow rate of 1 ml/min; (ii) amino acid analysis after peptide acidolysis [6 M HCl/2% (w/v) phenol, 20 h, 120° C., $N_2$ atmosphere]; and (iii) molecular mass determination by matrix-assisted laser desorption ionization-time of flight (MALDI-TOF) spectrometry. Some of the MS results are shown in Table 3 below and some of the HPLC profiles are shown in FIG. 1.

TABLE 3

Mass spectra of OsK1 and its derivatives

| Peptide | Theoretical | Experimental |
|---|---|---|
| OsK1 | 4205.24 | 4205.57 |
| [K16]-OsK1 | 4204.3 | 4204.64 |
| [D20]-OsK1 | 4192.15 | 4189.94 |
| AOsK1 | 4191.21 | 4192.02 |
| [P12]-AOsK1 | 4132.09 | 4132.00 |
| [Y36]-AOsK1 | 4253.28 | 4253.70 |
| Val-AOsK1 | 4290.26 | 4280.68 |

Electrophysiological experiments were carried out at 22-24° C. using the patch-clamp whole-cell recording mode. Cells were bathed with mammalian Ringer's solution (in mM): 160 NaCl, 4.5 KCl, 2 $CaCl_2$, 1 $MgCl_2$, and 10 HEPES (pH 7.4 with NaOH), with an osmolarity of 290-320 mOsm. When AOsK1 derivatives were applied, 0.1% bovine serum albumin was added to the Ringer's solution. A syringe-driven perfusion device was used to exchange the external recording bath solution. Two internal pipette solutions were used, one for measuring voltage-gated $K^+$ currents that contained (in mM): 155 KF, 2 $MgCl_2$, 10 HEPES, and 10 EGTA (pH 7.2 with KOH), with an osmolarity of 290-320 mOsm and another for measuring $Ca^{2+}$-activated $K^+$ currents that contained (in mM): 135 K-aspartate, 8.7 $CaCl_2$, 2 $MgCl_2$, 10 EGTA, 10 HEPES (pH 7.2 with KOH), with an osmolarity of 290-320 mOsm. A free $[Ca^{2+}]_i$ of 1 µM was calculated. All currents through voltage-gated $K^+$ channels were elicited by 200 ms depolarising voltage steps from −80 to +40 mV. Potassium currents through $K_{Ca}1.1$, $K_{Ca}2.1$ and $K_{Ca}3.1$ were elicited by 1 µM internal $[Ca^{2+}]_i$ and 400 ms voltage ramps from −120 to 0 mV (for $K_{Ca}3.1$ channel and $K_{Ca}1.1$ channel) and from −120 to +40 mV (for $K_{Ca}2.1$ channel). Electrodes were pulled from glass capillaries (Science Products, Germany), and fire-polished to resistances of 2.5-5 MΩ. Membrane currents were measured with an EPC-9 or EPC-10 patch-clamp amplifier (HEKA Elektronik, Lambrecht, Germany) interfaced to a Macintosh computer running acquisition and analysis software (Pulse and PulseFit). When voltage-gated $K^+$ currents were measured, the capacitive and leak currents were subtracted using a P/10 procedure. Series resistance compensation (>80%) was used for currents above 2 nA. The holding potential was −80 mV in all experiments. Data analyses were performed with Igor Pro (WaveMetrics, Oregon, USA), and $IC_{50}$ values were deduced by fitting a modified Hill equation to the data ($I_{toxin}/I_{control}=1/[1+([AOsK1\ analogue]/IC_{50})]$, where I is the peak current (for voltage-gated $K^+$ channels), or the slope of the ramp current, i.e. the conductance measured between −100 and −60 mV (for $Ca^{2+}$-activated $K^+$ channels) to the normalized data points obtained with four different AOsK1 analogue concentrations. The results are shown in Table 4.

TABLE 4

| Peptide | $ID_{50}$ mKv1.1 (nM) | $ID_{50}$ hKv1.2 (nM) | $ID_{50}$ mKv1.3 (nM) | $ID_{50}$ hKv3.2 (nM) | $ID_{50}$ hIK1 (nM) |
|---|---|---|---|---|---|
| OsK1 | 0.6 ± 0.04 | 5.4 ± 1.89 | 0.014 ± 0.001 | >1 µM | 225 ± 10 |
| OsK1-$NH_2$ | 0.3 ± 0.03 | 26 ± 6 | 0.019 ± 0.003 | >1 µM | >1 µM |
| Ac-OsK1-$NH_2$ | 1.33 ± 0.1 | ~1.3 µM | 0.075 ± 0.005 | >1 µM | >1 µM |
| [$\Delta^1$]-OsK1-$NH_2$ | 2.06 ± 0.2 | 85 ± 11 | 0.038 ± 0.003 | >1 µM | 620 ± 50 |
| [$A^{34}$]-OsK1 | 15.8 ± 2.8 | 65 ± 3 | 0.034 ± 0.008 | >1 µM | >1 µM |
| [$K^{16}$]-OsK1 | 0.63 ± 0.05 | 5.23 ± 0.22 | 0.067 ± 0.006 | n/a | 151 ± 21 |

TABLE 4-continued

| Peptide | ID$_{50}$ mKv1.1 (nM) | ID$_{50}$ hKv1.2 (nM) | ID$_{50}$ mKv1.3 (nM) | ID$_{50}$ hKv3.2 (nM) | ID$_{50}$ hIK1 (nM) |
|---|---|---|---|---|---|
| [D$^{20}$]-OsK1 | 2.95 ± 0.24 | 77.8 ± 9.2 | 0.037 ± 0.007 | n/a | 716 ± 1 |
| AOsK1 | 0.4 ± 0.01 | 2.96 ± 0.01 | 0.003 ± 0.001 | >1 μM | 228 ± 92 |
| Val-AOsK1 | 14.2 ± 1.3 | >1 μM | 0.328 ± 0.032 | n/a | >1 μM |
| AOsK1-NH$_2$ | 0.36 ± 0.04 | 19 ± 3 | 0.075 ± 0.006 | 1 ± 0.2 μM | >1 μM |
| [Δ$^1$]-AOsK1 | 0.19 ± 0.01 | 30 ± 7 | 0.025 ± 0.002 | 95 ± 10 | 425 ± 25 |
| [Δ$^1$]-AOsK1-NH$_2$ | 0.37 ± 0.02 | 41 ± ? | 0.067 ± 0.007 | >1 μM | >1 μM |
| [Δ$^1$, T$^2$]-AOsK1 | 0.36 ± 0.04 | 100 ± 5 | 0.021 ± 0.004 | 65 ± 10 | >1 μM |
| [Δ$^{1-4}$]-AOsK1 | 2.67 ± 0.5 | 245 ± 77 | 0.038 ± 0.001 | >1 μM | >1 μM |
| [Δ$^{1-6}$]-AOsK1 | 2.18 ± 0.3 | 634 ± 5 | 0.045 ± 0.002 | >1 μM | >1 μM |
| [Δ$^{1-7}$]-AOsK1 | 7.9 ± 1.2 | >1 μM | 0.114 ± 0.005 | >1 μM | >1 μM |
| [Δ$^{36-38}$]-AOsK1 | 366 ± 63 | >1 μM | 1.85 ± 0.7 | >1 μM | >1 μM |
| [K$^3$]-AOsK1-NH$_2$ | 0.2 ± 0.02 | 22 ± 4 | 0.100 ± 0.015 | >1 μM | >1 μM |
| [P$^{12}$]-AOsK1 | 3.18 ± 0.11 | 196 ± 13 | 0.059 ± 0.003 | n/a | 2600 ± 400 |
| [N$^{25}$]-AOsK1 | 791 ± 121 | 212 ± 3 | 5.4 ± 0.9 | >1 μM | >1 μM |
| [R$^{31}$]-AOsK1 | 0.28 ± 0.02 | 0.43 ± 0.03 | 0.045 ± 0.006 | 220 ± 20 | >1 μM |
| [Y$^{36}$]-AOsK1 | 34.4 ± 0.3 | 231.8 ± 0.1 | 0.122 ± 0.007 | n/a | 885 ± 18 |
| Ac-[K$^{12}$, R$^{19}$]-AOsK1 | 2.76 ± 0.4 | 101 ± 3 | 0.090 ± 0.004 | 1.5 ± 0.2 μM | >1 μM |

No activity was detected at micromolar concentrations for any of the synthesized peptides on voltage-gated channels hKv1.4, Kv1.5, hKv1.6, mKv1.7, mKv3.1 and hKv11.x (also referred to as HERG, human ether-a-go-go related gene) or on Ca$^{2+}$-activated K$^+$ channels hK$_{Ca}$1.1 (also referred to as BK) and hK$_{Ca}$2.1 (also referred to as SK1).

The peptides were evaluated for toxicity in vivo by determining the 50% lethal dose (LD$_{50}$) after intracerebroventricular injection into 20 g C57/BL6 mice. Groups of six to eight mice per dose were injected with 5 μl peptide solution containing 0.1% (w/v) bovine serum albumin and 0.9% (w/v) NaCl. The LD$_{50}$ values are set out in Table 5.

TABLE 5

| Peptide | LD$_{50}$ (μg/kg) |
|---|---|
| OsK1 | 2 |
| OsK1-NH$_2$ | 3.5 |
| Ac-OsK1-NH$_2$ | 11 |
| [Δ$^1$]-OsK1-NH$_2$ | 7 |
| [Δ$^{34}$]-OsK1 | 10 |
| [K$^{16}$]-OsK1 | 3 |
| [D$^{20}$]-OsK1 | 4.5 |
| AOsK1 | 2.5 |
| Val-AOsK1 | 16 |
| AOsK1-NH$_2$ | 2.25 |
| [Δ$^1$]-AOsK1 | 3 |
| [Δ$^1$]-AOsK1-NH$_2$ | 4.5 |
| [Δ$^1$, T$^2$]-AOsK1 | 3 |
| [Δ$^{1-4}$]-AOsK1 | 5 |
| [Δ$^{1-6}$]-AOsK1 | 6.5 |
| [Δ$^{1-7}$]-AOsK1 | 15 |
| [Δ$^{36-38}$]-AOsK1 | 800 |
| [K$^3$]-AOsK1 -NH$_2$ | 2.25 |
| [P$^{12}$]-AOsK1 | 7.5 |
| [N$^{25}$]-AOsK1 | 11.5 |
| [R$^{31}$]-AOsK1 | 5 |
| [Y$^{36}$]-AOsK1 | 9 |
| Ac-[K$^{12}$, R$^{19}$]-AOsK1 | 17.5 |

The effect of co-administering AOsK1 and MTx has been tested on Lewis rats immunized with spinal cord homogenate emulsified with complete Freund adjuvant. Each rat received 200 μl of emulsion sc, divided in the rear footpads, on day 0. Eight days later, as their body weight decreased, a precursor sign for clinical EAE, an osmotic pump was implanted IP. The pump delivered drugs at 1 μl/h for 8 days. They were filled with the peptide blockers, dissolved in Na Cl 0.15 M containing 2% Lewis serum, as vehicle.

Two additional groups of rats non-immunized were treated with the blockers in the same conditions. Blood samples were collected after 4 days of continuous administration in order to measure the blocker concentration in serum, using the patch-clamp technique.

Clinical evaluation. The severity of the disease was scored on a scale of 0 to 6, with 0.5 points for intermediate clinical findings (0: no clinical signs; 1.0: limp tail; 2.0: mild paraparesis and ataxia; 3.0: moderate paraparesis; 4.0: complete hind limb paralysis; 5.0: paralysis+incontinence; 5.5: tetraplegia; 6.0: moribund or death). Rats were weighed every day. Rats showing no clinical signs of EAE and no weight loss were excluded from the studies. The beneficial effects of K$^+$ blockers on EAE were evaluated by a reduction in clinical severity and in duration of the disease and in number of relapses compared with those of rats treated with the vehicle only, 0.15 M NaCl.

Data analysis. Statistical analysis was conducted using the Mann-Whitney U test. Mean differences between groups were considered significant at values of P<0.05.

Results are shown in Table 6. The combination of 50 nM of MTx and 50 nM of AOsK1 proved more effective than 50 nM of MT alone.

TABLE 6

MTX and AOsK1 treatment of chronic relapsing EAE

| | First episode of EAE | | | |
|---|---|---|---|---|
| Groups of rats | Onset (day)$^a$ | Duration (days)$^b$ | Max Clin Sc | Incid (%) |
| Vehicle | | | | |
| 1 | d9 | 10 | 4 | |
| 2 | d7 | 13 | 4 | |
| 3 | d7 | chronic | 5 | |
| 0 | d11 | 10 | 5 | |
| 5 | d8 | 13 | 5 | |
| Mean ± SD | | | 4.6 ± 0.5 | 100 |
| MTx 50 nM | | | | |
| 1 | d11 | chronic | 4 | |
| 2 | d8 | 11 | 1 | |

TABLE 6-continued

MTX and AOsK1 treatment of chronic relapsing EAE

| Groups of rats | First episode of EAE | | | |
|---|---|---|---|---|
| | Onset (day)[a] | Duration (days)[b] | Max Clin Sc | Incid (%) |
| 3 | d7 | chronic | 1 | |
| 0 (d) | d7 | chronic | 3 | |
| Mean ± SD | | | 2.2 ± 1.5* | 100 |
| MTX 50 nM AOsK1 50 nM | | | | |
| 1 | d11 | 4 | 1 | |
| 2 | d12 | 4 | 1 | |
| 3 | d11 | 3 | 0.5 | |
| Mean ± SD | | | 0.83 ± 0.2* | 100 |
| MTx 6.2 nM AOsK1 50 nM | | | | |
| 1 | d10 | 10 | 5 | |
| 2 | d12 | 7 | 5 | |
| 3[d] | d13 | 2 | 0.5 | |
| Mean ± SD | | | 3.5 ± 2.5 | 100 |

[a] day when first clinical signs (even scored 0.5) appear.
[b] number of days until clinical signs reverse to minimal score (0.5).
[c] aggravation
[d] 2 sd relapse
*Mean differences between groups were considered significant at values of $P < 0.05$ (Mann-Whitney U test).

---

The invention claimed is:

1. An OsK1 derivative selected from the group consisting of the following OsK1 derivatives:

[$\Delta^1$]-OsK1,
[$A^{34}$]-OsK1,
[$K^{16}$]-OsK1,
[$D^{20}$]-OsK1,
[$K^{16},D^{20}$]-OsK1,
[$\Delta^1,K^{16},D^{20}$]-OsK1,
[$\Delta^1,T^2,K^{16},D^{20}$]-OsK1,
[$\Delta^{1-4},K^{16},D^{20}$]-OsK1,
[$\Delta^{1-6},K^{16},D^{20}$]-OsK1,
[$\Delta^{1-7},K^{16},D^{20}$]-OsK1,
[$K^3,K^{16},D^{20}$]-OsK1,
[$P^{12},K^{16},D^{20}$]-OsK1,
[$K^{16},D^{20},N^{25}$]-OsK1,
[$K^{16},D^{20},R^{31}$]-OsK1,
[$K^{16},D^{20},Y^{36}$]-OsK1, and
[$K^{12}, K^{16},R^{19},D^{20}$]-OsK1.

2. An OsK1 derivative according to claim 1, which is terminated at the N-terminal with an acetyl group or which is amidated at the C-terminal.

3. An OsK1 derivative according to claim 1, which is terminated with an ω-amino-fatty acid having from 4 to 10 carbon atoms and from 0 to 2 carbon-carbon double bonds.

4. A pharmaceutical composition comprising an OsK1 derivative according to claim 1 in admixture with a pharmaceutically acceptable diluent or carrier.

5. An OsK1 derivative according to claim 1, wherein said derivative is [$\Delta^{1-7},K^{16},D^{20}$]-OsK1 (SEQ ID NO: 19).

6. An OsK1 derivative according to claim 1, wherein said derivative is [$K^{16},D^{20}$]-OsK1 (SEQ ID NO: 14).

* * * * *

SEQUENCE LISTING

<160> NUMBER OF SEQ ID NOS: 26

<210> SEQ ID NO 1
<211> LENGTH: 38
<212> TYPE: PRT
<213> ORGANISM: Androctonus mauretanicus

<400> SEQUENCE: 1

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 2
<211> LENGTH: 38
<212> TYPE: PRT
<213> ORGANISM: Leiurus quinquestriatus

<400> SEQUENCE: 2

Gly Val Pro Ile Asn Val Ser Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 3
<211> LENGTH: 38
<212> TYPE: PRT
<213> ORGANISM: Leiurus quinquestriatus

<400> SEQUENCE: 3

Gly Val Pro Ile Asn Val Pro Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys

-continued

```
                 35

<210> SEQ ID NO 4
<211> LENGTH: 38
<212> TYPE: PRT
<213> ORGANISM: Leiurus quinquestriatus

<400> SEQUENCE: 4

Gly Val Pro Ile Asn Val Lys Cys Thr Gly Ser Pro Gln Cys Leu Lys
1               5                   10                  15

Pro Cys Lys Asp Ala Gly Met Arg Phe Gly Lys Cys Ile Asn Gly Lys
            20                  25                  30

Cys His Cys Thr Pro Lys
        35

<210> SEQ ID NO 5
<211> LENGTH: 37
<212> TYPE: PRT
<213> ORGANISM: Androctonus mauretanicus

<400> SEQUENCE: 5

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Arg Lys Cys
            20                  25                  30

Asp Cys Thr Pro Lys
        35

<210> SEQ ID NO 6
<211> LENGTH: 37
<212> TYPE: PRT
<213> ORGANISM: Buthus martensi

<400> SEQUENCE: 6

Val Gly Ile Asn Val Lys Cys Lys His Ser Gly Gln Cys Leu Lys Pro
1               5                   10                  15

Cys Lys Asp Ala Gly Met Arg Phe Gly Lys Cys Ile Asn Gly Lys Cys
            20                  25                  30

Asp Cys Thr Pro Lys
        35

<210> SEQ ID NO 7
<211> LENGTH: 38
<212> TYPE: PRT
<213> ORGANISM: Orthochirus scrobiculosus

<400> SEQUENCE: 7

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 8
<211> LENGTH: 38
<212> TYPE: PRT
<213> ORGANISM: Artificial Sequence
<220> FEATURE:
<223> OTHER INFORMATION: Synthetic Construct

<400> SEQUENCE: 8
```

-continued

Gly Val Pro Ile Asn Val Lys Cys Arg Gly Ser Pro Gln Cys Ile Gln
1               5                   10                  15

Pro Cys Arg Asp Ala Gly Met Arg Phe Gly Lys Cys Met Asn Gly Lys
            20                  25                  30

Cys His Cys Thr Pro Gln
        35

<210> SEQ ID NO 9
<211> LENGTH: 34
<212> TYPE: PRT
<213> ORGANISM: Scorpio maurus

<400> SEQUENCE: 9

Val Ser Cys Thr Gly Ser Lys Asp Cys Tyr Ala Pro Cys Arg Lys Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 10
<211> LENGTH: 37
<212> TYPE: PRT
<213> ORGANISM: Artificial Sequence
<220> FEATURE:
<223> OTHER INFORMATION: Synthetic Construct

<400> SEQUENCE: 10

Val Ile Ile Asn Val Lys Cys Lys Ile Ser Arg Gln Cys Leu Glu Pro
1               5                   10                  15

Cys Lys Lys Ala Gly Met Arg Phe Gly Lys Cys Met Asn Gly Lys Cys
            20                  25                  30

His Cys Thr Pro Lys
        35

<210> SEQ ID NO 11
<211> LENGTH: 38
<212> TYPE: PRT
<213> ORGANISM: Artificial Sequence
<220> FEATURE:
<223> OTHER INFORMATION: Synthetic Construct

<400> SEQUENCE: 11

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys Ala Cys Thr Pro Lys
        35

<210> SEQ ID NO 12
<211> LENGTH: 38
<212> TYPE: PRT
<213> ORGANISM: Artificial Sequence
<220> FEATURE:
<223> OTHER INFORMATION: Synthetic Construct

<400> SEQUENCE: 12

Gly Val Ile Ile Asn Val Lys Cys Lys Ile Ser Arg Gln Cys Leu Lys
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 13
<211> LENGTH: 38
<212> TYPE: PRT
<213> ORGANISM: Artificial Sequence
<220> FEATURE:
<223> OTHER INFORMATION: Synthetic Construct

<400> SEQUENCE: 13

Gly Val Ile Ile Asn Val Lys Cys Lys Ile Ser Arg Gln Cys Leu Glu
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 14
<211> LENGTH: 38
<212> TYPE: PRT
<213> ORGANISM: Artificial Sequence
<220> FEATURE:
<223> OTHER INFORMATION: Synthetic Construct

<400> SEQUENCE: 14

Gly Val Ile Ile Asn Val Lys Cys Lys Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 15
<211> LENGTH: 37
<212> TYPE: PRT
<213> ORGANISM: Artificial Sequence
<220> FEATURE:
<223> OTHER INFORMATION: Synthetic Construct

<400> SEQUENCE: 15

Val Ile Ile Asn Val Lys Cys Lys Ile Ser Arg Gln Cys Leu Lys Pro
1               5                   10                  15

Cys Lys Asp Ala Gly Met Arg Phe Gly Lys Cys Met Asn Gly Lys Cys
            20                  25                  30

His Cys Thr Pro Lys
        35

<210> SEQ ID NO 16
<211> LENGTH: 37
<212> TYPE: PRT
<213> ORGANISM: Artificial Sequence
<220> FEATURE:
<223> OTHER INFORMATION: Synthetic Construct

<400> SEQUENCE: 16

Thr Ile Ile Asn Val Lys Cys Lys Ile Ser Arg Gln Cys Leu Lys Pro
1               5                   10                  15

Cys Lys Asp Ala Gly Met Arg Phe Gly Lys Cys Met Asn Gly Lys Cys
            20                  25                  30

His Cys Thr Pro Lys
        35

<210> SEQ ID NO 17
<211> LENGTH: 34
<212> TYPE: PRT
<213> ORGANISM: Artificial Sequence
<220> FEATURE:
<223> OTHER INFORMATION: Synthetic Construct

<400> SEQUENCE: 17

```
Asn Val Lys Cys Lys Ile Ser Arg Gln Cys Leu Lys Pro Cys Lys Asp
1               5                   10                  15
Ala Gly Met Arg Phe Gly Lys Cys Met Asn Gly Lys Cys His Cys Thr
            20                  25                  30
Pro Lys
```

<210> SEQ ID NO 18
<211> LENGTH: 32
<212> TYPE: PRT
<213> ORGANISM: Artificial Sequence
<220> FEATURE:
<223> OTHER INFORMATION: Synthetic Construct

<400> SEQUENCE: 18

```
Lys Cys Lys Ile Ser Arg Gln Cys Leu Lys Pro Cys Lys Asp Ala Gly
1               5                   10                  15
Met Arg Phe Gly Lys Cys Met Asn Gly Lys Cys His Cys Thr Pro Lys
            20                  25                  30
```

<210> SEQ ID NO 19
<211> LENGTH: 31
<212> TYPE: PRT
<213> ORGANISM: Artificial Sequence
<220> FEATURE:
<223> OTHER INFORMATION: Synthetic Construct

<400> SEQUENCE: 19

```
Cys Lys Ile Ser Arg Gln Cys Leu Lys Pro Cys Lys Asp Ala Gly Met
1               5                   10                  15
Arg Phe Gly Lys Cys Met Asn Gly Lys Cys His Cys Thr Pro Lys
            20                  25                  30
```

<210> SEQ ID NO 20
<211> LENGTH: 35
<212> TYPE: PRT
<213> ORGANISM: Artificial Sequence
<220> FEATURE:
<223> OTHER INFORMATION: Synthetic Construct

<400> SEQUENCE: 20

```
Gly Val Ile Ile Asn Val Lys Cys Lys Ile Ser Arg Gln Cys Leu Lys
1               5                   10                  15
Pro Cys Lys Asp Ala Gly Met Arg Phe Gly Lys Cys Met Asn Gly Lys
            20                  25                  30
Cys His Cys
        35
```

<210> SEQ ID NO 21
<211> LENGTH: 38
<212> TYPE: PRT
<213> ORGANISM: Artificial Sequence
<220> FEATURE:
<223> OTHER INFORMATION: Synthetic Construct

<400> SEQUENCE: 21

```
Gly Val Lys Ile Asn Val Lys Cys Lys Ile Ser Arg Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 22
<211> LENGTH: 38
<212> TYPE: PRT
<213> ORGANISM: Artificial Sequence
<220> FEATURE:
<223> OTHER INFORMATION: Synthetic Construct

<400> SEQUENCE: 22

```
Gly Val Ile Ile Asn Val Lys Cys Lys Ile Ser Pro Gln Cys Leu Lys
1               5                   10                  15

Pro Cys Lys Asp Ala Gly Met Arg Phe Gly Lys Cys Met Asn Gly Lys
            20                  25                  30

Cys His Cys Thr Pro Lys
        35
```

<210> SEQ ID NO 23
<211> LENGTH: 38
<212> TYPE: PRT
<213> ORGANISM: Artificial Sequence
<220> FEATURE:
<223> OTHER INFORMATION: Synthetic Construct

<400> SEQUENCE: 23

```
Gly Val Ile Ile Asn Val Lys Cys Lys Ile Ser Arg Gln Cys Leu Lys
1               5                   10                  15

Pro Cys Lys Asp Ala Gly Met Arg Asn Gly Lys Cys Met Asn Gly Lys
            20                  25                  30

Cys His Cys Thr Pro Lys
        35
```

<210> SEQ ID NO 24
<211> LENGTH: 38
<212> TYPE: PRT
<213> ORGANISM: Artificial Sequence
<220> FEATURE:
<223> OTHER INFORMATION: Synthetic Construct

<400> SEQUENCE: 24

```
Gly Val Ile Ile Asn Val Lys Cys Lys Ile Ser Arg Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35
```

<210> SEQ ID NO 25
<211> LENGTH: 38
<212> TYPE: PRT
<213> ORGANISM: Artificial Sequence
<220> FEATURE:
<223> OTHER INFORMATION: Synthetic Construct

<400> SEQUENCE: 25

```
Gly Val Ile Ile Asn Val Lys Cys Lys Ile Ser Arg Gln Cys Leu Lys
1               5                   10                  15
```

```
Pro Cys Lys Asp Ala Gly Met Arg Phe Gly Lys Cys Met Asn Gly Lys
            20                  25                  30

Cys His Cys Tyr Pro Lys
            35

<210> SEQ ID NO 26
<211> LENGTH: 38
<212> TYPE: PRT
<213> ORGANISM: Artificial Sequence
<220> FEATURE:
<223> OTHER INFORMATION: Synthetic Construct

<400> SEQUENCE: 26

Gly Val Ile Ile Asn Val Lys Cys Lys Ile Ser Lys Gln Cys Leu Lys
1               5                   10                  15

Pro Cys Arg Asp Ala Gly Met Arg Phe Gly Lys Cys Met Asn Gly Lys
            20                  25                  30

Cys His Cys Thr Pro Lys
            35
```